United States Patent [19]

Berg

[11] Patent Number: 5,051,153

[45] Date of Patent: Sep. 24, 1991

[54] SEPARATION OF METHYLENE CHLORIDE FROM METHYLAL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 702,970

[22] Filed: May 20, 1991

[51] Int. Cl.$^5$ .......................... B01D 3/40; C07C 17/38
[52] U.S. Cl. ......................................... 203/60; 203/62; 203/63; 568/594; 570/262
[58] Field of Search .............................. 203/60, 62, 63; 570/262; 568/594

[56] References Cited

U.S. PATENT DOCUMENTS

| | | | |
|---|---|---|---|
| 1,566,819 | 12/1925 | Carter | 568/594 |
| 3,222,262 | 12/1965 | Enk et al. | 568/594 |
| 4,263,102 | 4/1981 | Schorr et al. | 570/262 |

FOREIGN PATENT DOCUMENTS

| | | | |
|---|---|---|---|
| 142183 | 6/1980 | German Democratic Rep. | 203/64 |
| 59-76026 | 4/1984 | Japan | 570/262 |
| 61-93147 | 5/1986 | Japan | 570/262 |

*Primary Examiner*—Wilbur Bascomb, Jr.

[57] ABSTRACT

Methylal cannot be completely separated from methylene chloride by conventional distillation or rectification because of the maximum boiling azeotrope. Methylal can be readily separated from methylene chloride by extractive distillation. Typical effective agents are n-butyl acetate, diisobutyl ether and 4-methyl-2-pentanone.

1 Claim, No Drawings

SEPARATION OF METHYLENE CHLORIDE FROM METHYLAL BY EXTRACTIVE DISTILLATION

FIELD OF THE INVENTION

This invention relates to a method for separting methylene chloride from methylal using certain organic compounds as the agent in extractive distillation.

DESCRIPTION OF PRIOR ART

Extractive distillation is the method of separating close boiling compounds of azeotropes by carrying out the distillation in a multi-plate rectification column in the presence of an added liquid or liquid mixture, said liquid (s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Methylene chloride, B.P. = 40° C. forms a maximum boiling azeotrope with methylal, B.P. = 42.3° C. at 45° C. containing 41% methylene chloride. The methylene chloride - methylal azeotrope is impossible to separate by distillation because the relative volatility of an azeotrope is 1.0. Extractive distilation would be an attractive method of effecting the separation methylene chloride from methylal if agents can be found that (1) will enhance the relative volatlity between methylene chloride and methylal and (2) are easy to recover, that is, form no azeotrope with methylene chloride or methylal and boil sufficiently above these compounds to make separation by rectification possible with only a few theoretical plates.

Extractive distillation typically requires the addition of an equal amount to twice as much extractive agent as the methylene chloride-methylal on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with methylene chloride otherwise it will form a two-phase azeotrope with the methylene chloride in the recovery column and some other method of separation will have to be employed.

TABLE 1

Effect of Relative Volatility on the Separation of Methylal From Methylene Chloride at 99% Purity by Extractive Distillation

| Relative Volatility | Theoretical Plates | Actual Plates 75% Efficiency | Actual Plates 75% Eff., Min Reflux |
|---|---|---|---|
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent for this separation is shown in Table 1. Ordinary rectification cannot completely separate methylal from methylene chloride because of the maximum azeotrope. When extractive distillation is employed with an agent that converts the relative volatility to 1.5, only 31 actual plates are required.

OBJECTIVE OF THE INVENTION

The objects of this invention are to provide a process or method of extractive distillation that will enhance the relative volatility of methylal to methylene chloride in their separation in a rectification column. It is a further object of this invention to identify organic compounds that are stable, can be separated from methylene chloride by rectification with relatively few plates and can be recycled to the extractive distillation column with little decomposition.

SUMMARY OF THE INVENTION

The objects of this invention are provided by a process for the separation of methylal from methylene chloride which entails the use of certain organic compounds as the agent in extractive distillation.

DETAILED DESCRIPTION OF THE INVENTION

We have discovered that certain organic compounds will effectively increase the relative volatility between methylal and methylene chloride and permit the separation of methylal from methylene chloride by rectification when employed as the agent in extractive distillation. Table 2 lists the agents that we have found to be effective. The data in Tables 2 and 3 was obtained in a vapor-liquid equilibrium still. In every case, the starting mixture was the methylal - methylene chloride azeotrope. The relative volatilities are listed for each of the agents investigated. The compounds which are effective are methyl acetate, ethyl acetate, isopropyl acetate, n-propyl acetate, isobutyl acetate, n-butyl acetate, isoamyl acetate, n-amyl acetate, 3-pentanone, methyl isobutyl ketone, methyl isopropyl ketone, 4-methyl-2-pentanone 2-pentanone, 3,3-dimethyl-2-butanone, methyl ethyl ketone, methyl propionate, 2,2-methoxyethoxyethyl ether, diisobutyl ether, methyl valerate, ethyl valerate, vinyl t-butyl ether, methyl t-butyl ester and vinyl isobutyl ether.

Table 3 lists a number of compounds that proved to be ineffective as extractive distillation agents in the separation of methylal from methylene chloride. 4-Methyl-2-butanone whose relative volatility had been determined in the vapor-liquid equilibrium still was then evaluated in a glass perforated plate rectification column possessing 7.3 theoretical plates and the results listed in Table 4. After two hours of continuous operation, a relative volatility of 1.55 was obtained with this extractive agent.

THE USEFULNESS OF THE INVENTION

The usefulness or utility of this invention can be demonstrated by referring to the data presented in Table 2 and 4. All of the successful agents show that methylal can be separated from methylene chloride by extractive distillation in a rectification column and that the ease of separation as measured by relative volatility is considerable.

TABLE 2

Effect Agents For Separating Methylal From Methylene Chloride

| Compounds | Relative Volatility |
|---|---|
| Ethyl acetate | 1.2 |
| Methyl acetate | 2.1 |
| Isopropyl acetate | 1.2 |
| n-Propyl acetate | 2.0 |
| Isobutyl acetate | 1.6 |
| n-Butyl acetate | 2.0 |
| Isoamyl acetate | 1.2 |
| n-Amyl acetate | 1.2 |
| 3-Pentanone | 1.3 |
| Methyl isobutyl ketone | 1.3 |
| Methyl isopropyl ketone | 1.3 |
| 4-Methyl-2-pentanone | 1.55 |
| 2-Pentanone | 1.6 |
| 3,3-Dimethyl-2-butanone | 1.5 |
| Methyl ethyl ketone | 1.3 |
| Methyl propionate, | 1.3 |
| 2,2-Methoxyethoxyethyl ether | 1.5 |
| Diisobutyl ether | 1.9 |
| Methyl valerate | 1.5 |
| Ethyl valerate | 1.3 |
| Vinyl n-butyl ether | 1.3 |
| Methyl t-butyl ether | 1.6 |
| Vinyl isobutyl ether | 1.7 |

TABLE 3

| Ineffective Agents | |
|---|---|
| Vinyl acetate | Methyl vinyl acetate |
| Methyl amyl acetate | Ethylene glycol methyl ether acetate |
| 3-Methyl-2-butanone | 2,2-Dimethoxy propane |
| Dimethyl carbonate | |

TABLE 4

| | Data From Run Made In Rectification Column | | | |
|---|---|---|---|---|
| Agent | Column | Time hrs. | Weight % Methylal | Weight % $CH_2Cl_2$ | Relative Volatility |
| 4-Methyl-2-pentanone | Overhead | 1 | 90 | 10 | 1.36 |
| | Bottoms | | 48.7 | 51.3 | |
| 4-Methyl-2-pentanone | Overhead | 2 | 96.7 | 3.3 | 1.55 |
| | Bottoms | | 54.6 | 45.4 | |

WORKING EXAMPLES

Example 1

Eighty grams of the methylal - methylene chloride azeotrope and 30 grams of n-propyl acetate were charged to a vapor-liquid equilibrium still and refluxed for six hours. Analysis indicated a vaor composition of 62.5% methylal, 37.5% methylene chloride; a liquid composition of 45.2% methylal, 54.8% methylene chloride which is a relative volatility of methylal to methylene chloride of 2.0.

Example 2

A solution comprising 118 grams of methylal and 82 grams methylene chloride was placed in the stillpot of a 7.3 theoretical plate rectification column. When refluxing began, an extractive agent comprising 4-methyl-2-pentanone was pumped into the column at a rate of 15 ml/min. The temperature of the extractive agent as it entered the column was 65° C. After establishing the feed rate of the extractive agent, the heat input to the methylal - methylene chloride in the stillpot was adjusted to give a total reflux rate of 40 ml/min. After two hours of operation at total reflux, overhead and bottoms samples of approximately two ml. were colected and analysed. The overhead analysis was 96.7% methylal, 3.3% methylene chloride and the bottoms analysis was 54.6% methylal, 45.4% methylene chloride. This give an average relative volatility of 1.55 for each theoretical plate. This data is presented in Table 4.

We claim:

1. A method for recovering methylal from a mixture of methylal and methylene chloride which comprises distilling a mixture of methylal and methylene chloride in the presence of about one part of an extractive agent per part of methylal- methylene chloride mixture, recovering methylal as overhead product and obtaining the methylene chloride and the extractive agent from the stillpot, wherein said extractive agent consists of one material selected from the group consisting of methyl acetate, ethyl acetate, isopropyl acetate, n-propyl acetate, isobutyl acetate, n-butyl acetate, isoamyl acetate, n-amyl acetate, 3-pentanone, methyl isobutyl ketone, methyl isopropyl ketone, 4-methyl-2-pentanone, 2-pentanone, 3,3-dimethyl-2-butanone, methyl ethyl ketone, methyl propionate, 2,2-methoxyethoxyethyl ether, diisobutyl ether, methyl valerate, ethyl valerate, vinyl n-butyl ether, methyl t-butyl ether and vinyl isobutyl ether.

* * * * *